__United States Patent__ [19]

Stiros

[11] 4,338,211

[45] Jul. 6, 1982

[54] LIQUID SURFACTANT SKIN CLEANSER WITH LATHER BOOSTERS

[75] Inventor: Paul Stiros, Maineville, Ohio

[73] Assignee: The Procter & Gamble Company, Cincinnati, Ohio

[21] Appl. No.: 252,691

[22] Filed: Apr. 9, 1981

Related U.S. Application Data

[63] Continuation-in-part of Ser. No. 164,702, Jun. 30, 1980, abandoned.

[51] Int. Cl.$^3$ .................... C11D 1/831; C11D 3/20; C11D 3/46; C11D 17/08
[52] U.S. Cl. .................................. 252/142; 252/136; 252/143; 252/153; 252/173; 252/541; 252/548; 252/550; 252/551; 252/DIG. 5; 252/DIG. 14
[58] Field of Search ............... 252/DIG. 5, DIG. 13, 252/DIG. 14, 153, 142, 143, 173, 529, 530, 531, 548, 541, 550, 551

[56] References Cited

U.S. PATENT DOCUMENTS

| | | | |
|---|---|---|---|
| 2,462,758 | 2/1949 | Malkemus | 252/161 |
| 2,607,740 | 8/1952 | Vitale et al. | 252/152 |
| 2,879,231 | 3/1959 | Allen et al. | 252/90 |
| 3,533,955 | 10/1970 | Pader et al. | 252/153 |
| 3,793,233 | 2/1974 | Rose et al. | 252/547 |
| 3,943,234 | 3/1976 | Roggenkamp | 252/142 |
| 4,130,497 | 12/1978 | Oneto et al. | 252/89 |
| 4,151,105 | 4/1979 | O'Roark | 252/145 |

FOREIGN PATENT DOCUMENTS

19970  12/1980  European Pat. Off. .

OTHER PUBLICATIONS

Schwartz et al., *Surface Active Agents & Detergents*, vol. 11, 1958, Interscience Publishers, N.Y., pp. 115-117 and 316.
Hart, J. R.: "Sarcosinate Surfactants in Skin Cleansers," *Cosmetic Technology*, Jan. 1980, pp. 41-44.
Garrett, H. E.: *Surface Active Chemicals*, Pergamon Press, New York, 1972, pp. 44-48.
Sanders et al., "Foam Stabilization by Alkylolamides", Soap & Sanitary Chemicals, vol. 29, No. 6, Jun. 1973, pp. 45-48 and 93.

*Primary Examiner*—Dennis L. Albrecht
*Attorney, Agent, or Firm*—Richard C. Witte; Ronald L. Hemingway; Leonard Williamson

[57] ABSTRACT

A liquid skin cleanser composition with improved lathering characteristics, comprising:
(A) 5-30 weight percent anionic surfactant selected from the group consisting of fatty alkyl sulfates, fatty alkyl ether sulfates and mixtures thereof;
(B) 0.5-12 weight percent of a lather boosting mixture consisting essentially of free fatty acids, fatty alkylol amide having a ratio of 1:3 to 3:1,
(C) water;

wherein said free fatty acids have a carbon atom chain length of from 8 to 18 and wherein said fatty acids consist of at least 25% of carbon chain lengths of less than 14, and wherein said lather boosting mixture is present in an amount equal to 10% to 40% of the weight to the surfactant, and wherein said composition has a pH of from about 4.0 to about 7.0.

12 Claims, No Drawings

LIQUID SURFACTANT SKIN CLEANSER WITH LATHER BOOSTERS

CROSS-REFERENCE TO RELATED APPLICATION

This application is a continuation-in-part of U.S. Ser. No. 164,702, filed by the present inventor June 30, 1980, now abandoned.

BACKGROUND OF THE INVENTION

This invention relates to liquid skin cleansers. More particularly, this invention relates to liquid skin cleansers comprising surfactants and lather boosters.

The cleaning of skin with surface-active cleaning preparations has become a focus of great interest. Many people wash and scrub their skin with various surface active preparations several times a day. Skin cleansers should cleanse the skin gently, causing little or no irritation, without defatting and drying the skin after frequent routine use. Certain synthetic surfactants are particularly mild. However, a major drawback of mild liquid synthetic surfactant systems when formulated for skin cleansing is poor lather performance. Compared to the highest bar soap standards (bars which are rich in coconut soap and super fatted), these prior art liquid surfactant formulations have either poor lather or poor skin mildness performance. As may be expected the lather performance is a function of the choice of surfactant and its concentration. The conceivable number of liquid surfactant compositions formulated with or without skin feel agents are numerous. Rheological and phase properties exhibited by prototypes vary widely (i.e., thin liquids, gels, thick pastes, solutions, emulsions). The phase stability of prototypes is for the most part acceptable over short time periods, but only a small fraction of them will maintain their original properties and acceptability over an extended period of time.

Optimization of lather as a single variable is a fairly straightforward process. The use of known high sudsing anionic surfactants with lather boosters yields acceptable lather volume. Unfortunately, highest sudsing anionic surfactants are, generally, also highest in skin oil removal and are worst in clinical mildness. Surfactants that are among the mildest with minimal skin oil removal, such as ammonium lauryl ether (12 EO) sulfate ($NH_4AE_{12}S$) are extremely poor in lather. These two facts make the surfactant selection and the lather boosting optimization process a delicate balancing act.

The ability of relatively small amounts of certain solubilized organic compounds to increase the foaming power of the fatty alkyl sulfates has been recognized for a long time. It is well known, for example, that in sulfating lauryl alcohol with chlorosulfonic acid, the use of excess sulfating agent will result in a product having very poor foam stability, and that the addition of free lauryl alcohol to this product will restore the foaming power. Lauryl alcohol is, accordingly, a foam-promoting builder for lauryl sulfate, and the high-foaming grades of commercial lauryl sulfates have always, since the first time produced in quantity, contained a small portion of lauryl alcohol. This proportion usually varies between 2% and 10% of the lauryl sulfate present and the precise content of lauryl alcohol is frequently a purchasing specification for lauryl sulfate detergents.

Lauryl alcohol and other members of the fatty alcohol series are also foam builders for certain other detergents, although they are reported not to be effective when used with the alkyl aromatic sulfonates. In general, the foam-building effect is highly specific, and materials which build the foam of one type of detergent may have little or no effect on another type. Another important characteristic of foam builders is that their effect varies considerably with the concentration. An excessive amount of a foam builder, relative to the amount of surfactant present, may actually have a foam-suppressing effect. The fatty monoethanolamides have been claimed and used commercially as foam builders for fatty alkyl sulfates. In practice lauryl or coconut monoethanolamide is used since they are much more effective than the higher members of the series.

The fatty diethanolamides have been favored as foam builders for the alkylarylsulfonates (British Pat. No. 693,063 to Colgate-Palmolive Peet Company). Coconut-oil fatty diethanolamide is said to be particularly effective, and has been widely used as a foam builder. This latter product is known to contain besides the fatty diethanolamide, some free fatty acid and amino fatty esters (H. L. Sanders and E. L. Knaggs, *Soap and Sanit. Chemicals,*, 29, No. 6, 45–8 (1953)). The fatty alkylol amides have also been used with soaps to promote and stabilize foams (Zussman et al., *Soap and Sanit. Chemicals,* 26, No. 4, 37–40, 141 (1950)).

U.S. Pat. No. 2,879,231, Allen et al., issued Mar. 24, 1959, relates to shampoos which may contain fatty acids and amides. E.g., in U.S. Pat. No. 4,151,105, J. R. O'Roark, issued Apr. 24, 1979. O'Roark's solid bar soap, however, requires from 10–30% paraffin, 5–15% starch and 10–30% dextrin, which is undesirable for liquid skin cleansers. Coconut-oil fatty acid is used to promote the plasticity and improved sudsing in a low pH synthetic bar soap. The coconut-oil fatty acid is used with lauric diethanolamide to supplement the coconut fatty acid.

In short, the rather stringent requirements for skin cleansers limit the choice of surface-active agents, and final formulations represent some degree of compromise. Mildness is often obtained at the expense of effective cleaning, or lathering may be sacrificed for either mildness, product stability, or both.

The present invention offers a valuable combination of desirable properties to liquid skin-cleaning formulations.

Therefore, one object of this invention is the development of liquid skin cleaning compositions which exhibit mild surface-acting and good lathering properties.

Another object of the present invention is the development of low cost liquid skin cleansers.

Other objects will become apparent from the detailed description below.

SUMMARY OF THE INVENTION

A liquid surfactant composition comprising:

(A) 5–30 weight percent anionic surfactant selected from the group consisting of fatty alkyl sulfates, fatty alkyl ether sulfates and mixtures thereof;

(B) 0.5–12 weight percent of a lather boosting mixture consisting essentially of free fatty acids, fatty alkylol amide having a ratio of 1:3 to 3:1;

(C) water;

wherein said free fatty acids have a carbon atom chain length of from 8 to 18 and wherein said fatty acids consist of at least 25% of carbon chain lengths of less than 14, and wherein said lather boosting mixture is present in an amount equal to 10% to 40% of the weight to the surfactant, and wherein said composition has a pH of from about 4.0 to about 7.0, is disclosed as a superior, mild synthetic, liquid skin cleanser with increased lather performance.

DETAILED DESCRIPTION OF THE INVENTION

This invention relates to fatty alkyl and ethoxylated alkyl sulfate surfactant liquid skin cleaning compositions with optimum lather performance. To illustrate: coconut-oil alkylol amides well known for their suds boosting power, have been used with said surfactants to provide improved lather. This invention, however, further enhances this lather boosting power of the amide by the use of coconut-oil fatty acid as a co-booster. The combination of the two boosters, coconut-oil alkylol amides and coconut-oil fatty acid, is synergistic in that at the same total level of booster use, the combination yields better lather performance in terms of volume with a rich creamy consistency than either component used alone at that level.

Specifically, a liquid surfactant composition comprising:

(A) 5-30 weight percent anionic surfactant selected from the group consisting of fatty alkyl sulfates, fatty alkyl ether sulfates and mixtures thereof;

(B) 0.5-12 weight percent of a lather boosting mixture consisting essentially of free fatty acids, fatty alkylol amide having a ratio of 1:3 to 3:1;

(C) water;

wherein said free fatty acids have a carbon atom chain length of from 8 to 18 and wherein said fatty acids consist of at least 25% of carbon chain lengths of less than 14, and wherein said lather boosting mixture is present in an amount equal to 10% to 40% of the weight to the surfactant, and wherein said composition has a pH of from about 4.0 to about 7.0, is disclosed as a superior, mild synthetic, liquid skin cleanser with increased lather performance.

SURFACTANT

One essential component of the liquid skin cleanser composition is a surfactant. The term "surfactant" as used herein is intended to denote a synthetic anionic surfactant. The surfactants of this invention are the alkali metal (e.g., sodium or potassium) and ammonium, alkyl sulfates derived by sulfation of $C_8$ to $C_{22}$ alcohols, either synthetically derived or produced by reduction of glycerides of tallow or coconut oil; and the alkali metal and ammonium salts of the sulfuric acid esters of the reaction product of 1 mole of a $C_8$ to $C_{22}$ alcohol (e.g., tallow or coconut oil alcohols) and about 1 to 20, preferably 1 to 13, moles of ethylene oxide (ethoxy groups). These are referred to herein, respectively, as alkyl sulfate and alkyl ether sulfate surfactants.

The preferred surfactants for use in the present compositions include ammonium or sodium lauryl sulfate and ammonium or sodium lauryl ether sulfate or combinations thereof. Preferred single surfactants are the alkyl ether sulfates with 1 to 6 ethoxy groups, especially ammonium and sodium lauryl ether sulfates. Preferred mixture of surfactants includes ammonium and/or sodium lauryl sulfate with ammonium and/or sodium lauryl ether sulfates. The surfactant level is between 5% and 30%, preferably between 10% and 25%, and most preferably 12-22%.

LATHER BOOSTERS

The lather boosting mixture consists essentially of free fatty acid and fatty alkylol amide having a ratio of 1:3 to 3:1 and preferably 1:2 to 2:1 and most preferably about 1:1. The lather boosting mixture is present at a level of from about 10% to 40% (most preferably 10-30%) by weight of the level of surfactant present.

Optimization of lather as a single variable is a fairly straightforward process. The use of high sudsing surfactants with lather boosters such as fatty acids, fatty alcohols, and fatty alkylolamides yields maximum lather volume. Unfortunately, high sudsing anionic surfactants generally also have the highest in skin oil removal and are the worst in clinical mildness. As mentioned previously, these two attributes (mildness and low sebum removal) are important performance characteristics of the preferred embodiment of this invention. Surfactants that are mildest with respect to minimum skin oil removal, such as $NH_4AE_{12}S$ (ammonium lauryl ether (12 EO) sulfate) are extremely poor in lather. These conflicting factors (mildness vs. lather) make the surfactant selection and lather optimization process a balancing act. By selecting the appropriate ratio of mild surfactant, high sudsing surfactant and utilizing materials that stabilize the foam film, a most preferred embodiment which not only has better lather performance compared to prior art liquid soap formulations but which is also relatively milder, is obtained.

The skin cleanser of this invention is excellent for hand lathering, but under heavy soil conditions, or when very dilute, as in the shower, the lather performance drops off relative to super-fatted bars containing a high proportion (50%) of coconut soap. However, even under those conditions, the cleanser of this invention is superior to marketplace liquid soaps. This drop-off in performance is a simple function of the built-in reduced detergency of the formula. However, the overall lather performance delivered by the compositions of this invention is superior to most bar soaps and marketplace liquid soaps.

FATTY ACID

The fatty acid components of the present composition are fatty acids having carbon atom chain lengths of anywhere from 8 to 18, wherein at least 25% (preferable at least 50%) by weight of the fatty acids have carbon atom chain lengths of less than 14.

The fatty acid is preferably a double distilled coconut-oil fatty acid having an iodine value ranging from about 6 to about 14. A suitable coconut-oil fatty acid consists by weight, for example, of 15% capric and caprylic acids, 48% lauric acid, 18% myristic acid, 9% palmitic acid, 2% stearic acid, 6% oleic acid, and 2% linoleic acid.

The fatty acid used as a co-booster with the alkylol amides improves the overall sudsing performance by increasing the lather.

ALKYLOL AMIDES

Higher fatty acid alkylolamide material has been found to exhibit improved lather creaminess when used with the above surfactants, particularly in the stability of the foam generated during the skin washing operation. The acyl radical of the alkylolamide is selected from the class of fatty acids having 8 to 20 carbons and each alkylol group has up to 3 carbon atoms usually. The amide can be either a dialkylol or monoalkylol amide. It is preferred to use the diethanolamides, di- or monoisopropanolamides and monoethanolamides of fatty acids having about 10 to 14 carbons in the alkyl radical. Examples are lauric, capric, myristic and coconut mono- and diethanolamides, and mixtures thereof. There may be employed also the alkylolamides which are substituted by addition of ethylene oxide groups, suitable examples being the above monoethanolamides, diethanolamides, and isopropanolamides condensed with 1 or 2 moles of ethylene oxide.

The solids content of the liquid product is variable and is usually from about 7% to 40% by weight of the composition, and the balance being primarily water. The ingredients are proportioned in the aqueous solubilizing medium so as to form a substantially homogeneous product of desired physical properties.

AQUEOUS CARRIER

The skin cleansers herein are preferably in the form of liquids or creams in which water is the principal diluent. The level of water in the compositions is typically from about 60% to about 93% by weight, preferably from 70–85%. Purified (distilled) water is preferred.

PH ADJUSTMENT AGENT

The pH of the liquid skin cleanser compositions herein should lie in the range of about 4.0 to about 7.0, preferably in the range of about 5.0 to about 6.0. The pH is kept in the acidic range to maintain the fatty acid in an unsaponified state. Suitable pH adjustment agents include HCl, citric acid, phosphoric acid, succinic acid and a sodium citrate/citric acid combination, among many others.

OPTIONAL COMPONENTS

The skin cleansers herein can contain a variety of nonessential optional ingredients suitable for improving such compositions in a variety of ways. Such conventional optional ingredients are well known to those skilled in the art, e.g., preservatives such as benzyl alcohol, methyl paraben, propyl paraben, 3-isothiazolinones (Kathon CG sold by Rohm and Haas) and imidazolidinyl urea can be used in amounts of from 1 to 5,000 ppm; thickeners and viscosity modifiers such as polyethylene glycols, sodium chloride, ammonium chloride, sodium sulfate, carboxymethyl cellulose, methylcellulose, polyvinyl alcohol, and ethyl alcohol; suspending agents such as magnesium/aluminum silicate; perfumes, dyes; opacifiers such as behenic acid, ethylene glycol distearate and calcium stearate; sequestering agents such as disodium ethylenediamine tetraacetate; emollients, moisturizers and various other skin treating ingredients such as glycerin; buffers and builders such as citrates and phosphates; lather modifying agents such as polymers, i.e., polyacrylamides and cationic polymeric derivatives such as JR 400 ® sold by Union Carbide. If present, such agents individually generally comprise from about 0.01% to about 5.0% by weight of the composition.

Additional surfactants can also be added as optional components to the present compositions. The optional surfactants may be selected from any of the other types of surfactants but the preferred types are nonionics and amphoterics.

A minor amount of a fatty alcohol may be employed as an optional ingredient. The alcohol may serve a multiplicity of functions such as improving lather characteristics, e.g., volume and creaminess. Surfactants made from fatty alcohols often contain some free fatty alcohol.

METHOD OF MANUFACTURE

The liquid skin cleanser compositions of the present invention are made using mixing techniques disclosed herein. A method of making the present invention is shown in the examples which follow.

COMPOSITION USE

In its method aspect, the present invention comprises a method of washing the skin by contacting the skin with an amount of the cleanser compositions herein which is effective to clean the skin and rinsing the cleanser from the skin. An effective amount for any individual will depend upon variable factors such as amount of soil on the skin, type of soil on the skin, level of surfactant in the cleanser composition, etc. Generally, an effective amount will be from about 0.5 to about 5 grams per use.

The following examples will illustrate the invention, but are not intended to be in any way limiting thereof.

| Ingredient | Wt. % |
|---|---|
| Purified Water | 71.3 |
| Ammonium Alkyl* Sulfate | 20.0 |
| Coconut Fatty Acid | 2.0 |
| Coconut Monoethanolamide | 2.0 |
| Glycerine | 3.0 |
| JR 400** | 0.5 |
| Ethylene Glycol Distearate | 1.0 |
| Fragrance | 0.2 |
| TOTAL | 100.0 |

*Derived from fatty alcohols with average straight chains of 12 to 14 carbon atoms.
**A cationic cellulosic polymer marketed by Union Carbide.

The liquid skin cleanser composition of Example I is preferred for its overall high lather volume performance.

EXAMPLE II

| Ingredient | Wt. % |
|---|---|
| Purified Water | 72.3 |
| Ammonium Alkyl* Ether Sulfate (ethoxylated with one mole ethylene oxide) | 20.0 |
| Coconut Fatty Acid | 1.5 |
| Coconut Monoethanolamide | 1.5 |
| Glycerine | 3.0 |
| JR 400 | 0.5 |
| Ethylene Glycol Distearate | 1.0 |
| Fragrance | 0.2 |
| TOTAL | 100.0 |

*Derived from fatty alcohols with average straight chains of 12 to 14 carbon atoms.

This Example II is most preferred for optimum lather/surfactant mildness balance.

EXAMPLE III

| Ingredient | Wt. % |
|---|---|
| Purified Water | 70.3 |
| Ammonium Alkyl* Sulfate | 6.7 |
| Ammonium Alkyl* Ether Sulfate (ethoxylated with 12 moles of ethylene oxide) | 11.0 |
| Alkyl Glyceryl Ether Sulfonate | 2.3 |
| Coconut Fatty Acid | 2.5 |
| Coconut Monoethanolamide | 2.5 |

-continued

| Ingredient | Wt. % |
|---|---|
| Glycerine | 3.0 |
| JR 400 | 0.5 |
| Ethylene Glycol Distearate | 1.0 |
| Fragrance | 0.2 |
| TOTAL | 100.0 |

*Derived from fatty alcohols with average straight chains of 12 to 14 carbon atoms.

Example III is the preferred composition for mildness.

EXAMPLE IV

A method which can be used to make the exemplary compositions of the present invention is as follows:

1. The surfactant(s) and purified water are mixed together at ambient temperature.
2. Glycerine addition follows.
3. The coconut fatty acid and coconut monoethanolamide are added simultaneously to the mixture with agitation.
4. The ethylene glycol distearate is added.
5. The batch is then heated to about 150° F.–160° F. (65°–70° C.) and becomes quite fluid.
6. The JR 400 (a cationic cellulosic polymer) is added slowly exercising care to disperse the polymer solids as evenly as possible.
7. A mixing period of 20 minutes is required to dissolve all the ingredients and to obtain a clear solution.
8. The formula pH is adjusted to 5.0 using hydrochloric acid.
9. The product is cooled to ambient temperature and fragrance is added.

The lather boosters are preferably added simultaneously. This may be done at room temperature or by the addition of previously co-melted boosters to the preheated surfactant mix.

Hand Lather Volume Evaluation Method Used

1. The hands are thoroughly washed to remove natural surface oils or other soils. This standardizes the hands to the same initial baseline condition before each series of evaluations.
2. The hands are dried.
3. The hands are then wet with warm water (97° F., 7 grain).
4. One (1) ml. of liquid product is placed into the palm of one hand.
5. The hands are rotated 10 times (10–15 sec. time span) to produce lather.
6. The lather on the hands is gently rinsed with 100 mls. of cool, distilled water into a wide mouth graduated cylinder. After rinsing is completed, there is a one minute wait before the lather is measured to allow excess water to drain from the suds. The lather height is read on the graduated cylinder and the volume of lather above the water level is recorded.
7. The hands are thoroughly rinsed and Steps 2–6 are repeated for each successive evaluation.

Hand Lather Weight Evaluation

This method is very similar to the lather volume evaluation with the following modifications:

1. The standard graduated cylinder is replaced with a graduated cylinder with a stopcock.
2. Prior to Step 6, the tare weight of the cylinder is found.
3. Following the recording of the lather volume in Step 6, the water in the bottom of the cylinder is drained through the stopcock.
4. The cylinder is then weighed. Subtracting the cylinder tare weight from this gives the weight of the lather.

In the following examples $NH_4AS$, $NH_4AE_1S$, $NH_4AE_{12}S$, AGS, CnFA and CnMEA symbolize, respectively, ammonium alkyl sulfate, ammonium alkyl ether (1 and 12 ethoxy groups respectively) sulfate, sodium alkyl glyceryl ether sulfonate, coconut monoethanol amide and coconut fatty acid. The alkyl radicals of all ingredients were derived from fatty alcohols with average carbon atom chain lengths of 12–14.

EXAMPLES V–X

| Ingredient | V Wt. % | VI Wt. % | VII Wt. % | VIII Wt. % | IX Wt. % | X Wt. % |
|---|---|---|---|---|---|---|
| $NH_4AS$ | 8.0 | 6.6 | 6.6 | 6.6 | 6.6 | 6.6 |
| $NH_4AE_{12}S$ | 14.0 | 11.0 | 11.0 | 11.0 | 11.0 | 11.0 |
| AGS | 3.0 | 2.4 | 2.4 | 2.4 | 2.4 | 2.4 |
| CnFA | — | 5.0 | — | 2.5 | 1.67 | 3.33 |
| CnMEA | — | — | 5.0 | 2.5 | 3.33 | 1.67 |
| Water | 75.0 | 75.0 | 75.0 | 75.0 | 75.0 | 75.0 |
|  | 100.0 | 100.0 | 100.0 | 100.0 | 100.0 | 100.0 |
| Hand Lather (Vol. ml.) | 180 | 220 | 230 | 270 | 240 | 250 |

TABLE I

| Hand Lather Volume | |
|---|---|
| Example V | 180 mls. |
| Example VI | 220 mls. |
| Example VII | 230 mls. |
| Example VIII | 270 mls. |
| Example IX | 240 mls. |
| Example X | 250 mls. |

The total weight percent of surfactant plus lather boosters used in each of Examples V–VIII was 25 wt.%. Note the synergistic lather co-boosting benefit of the compositions (Example VIII–X) in terms of creamy lather volume which illustrate preferred liquid skin cleanser compositions of this invention.

EXAMPLES A–F

The base formula of Examples A–F is: 13% $NH_4$-$E_1S$, 2% glycerin, 0.375% Na citrate, 0.225% citric acid and 0.2% ethylene diaminetetraacidic acid. Examples C–E, which are illustrations of this invention, all show improved lather performance in terms of volume with creamy consistency over Examples A, B and F.

TABLE II

| | Formula Codes | | | | | |
|---|---|---|---|---|---|---|
| Ingredient | A | B | C | D | E | F |
| % CnFA | — | 2.0 | 1.5 | 1.0 | 0.5 | — |
| % CnMEA | — | — | 0.5 | 1.0 | 1.5 | 2.0 |
| Hand Lather Evaluation | | | | | | |
| Volume, mls | 158 | 218 | 225 | 198 | 192 | 148 |
| Creaminess-weight, gms | 11.6 | 14.6 | 16.7 | 17.0 | 14.8 | 11.8 |
| density, gms/m/x$10^2$ | 7.3 | 6.6 | 7.4 | 8.6 | 7.7 | 8.0 |

The formula with no foam booster (A) has a low lather volume of 158. The formula with acid booster only (B) has a high lather volume of 218, but has the poorest lather in terms of creaminess as shown by a density of only 6.6. The formula with amide booster only (F) has a creamy lather density of 8.0, but exhibits the poorest lather volume of 148. It will be noted that formulas C, D and E of this invention provide improved skin cleansers in terms of creamy lather volume. Formulas C, D and E respectively show lather volumes of 225, 198 and 192 which are all higher than the 148 volume of formula (F) which contains only the amide booster. Formulas C, D and F also exhibit creamy lather densities of respectively 7.4, 8.6 and 7.7, which are all creamier than the 6.6 lather density of formula (B) which contains only the acid booster.

I claim:

1. A liquid skin cleanser composition comprising:
   (A) about 5–30 weight percent anionic surfactant selected from the group consisting of fatty alkyl sulfates, fatty alkyl ether sulfates and mixtures thereof;
   (B) about 0.5–12 weight percent of a lather boosting mixture consisting essentially of free fatty acids, fatty alkylol amide having a ratio of about 1:3 to about 3:1; and
   (C) water;
wherein said free fatty acids have a carbon atom chain length of from 8 to 18 and wherein said fatty acids consist of at least about 25% of carbon chain lengths of less than 14, and wherein said lather boosting mixture is present in an amount equal to about 10% to about 40% of the weight to the surfactant, and wherein said composition has a pH of from about 4.0 to about 7.0.

2. A liquid skin cleanser composition according to claim 1 wherein said lather boosting mixture has a ratio of about 2:1 to about 1:2 and is present at a level of from about 15% to about 30% by weight of the total surfactant present.

3. A liquid skin cleanser composition according to claim 2 wherein said free fatty acids consist of at least 50% by weight of fatty acids having carbon atom chain lengths of less than 14.

4. A liquid skin cleanser composition according to claim 3 wherein said alkylol amide is coconut monoethanolamide.

5. A liquid skin cleanser composition according to claim 4 wherein the surfactant is selected from the group consisting of ammonium lauryl sulfate, sodium lauryl sulfate, ammonium lauryl ether sulfate, sodium lauryl ether sulfate and mixtures thereof.

6. A liquid skin cleanser composition according to claim 5 wherein the pH is from about 5.0 to about 6.0.

7. A liquid skin cleanser composition according to claim 6 wherein the boosting mixture is present in an amount of from about 10% to about 30% of the weight of the surfactant.

8. A liquid skin cleanser composition according to claim 7 wherein the surfactant is ammonium lauryl sulfate.

9. A liquid skin cleanser composition according to claim 7 wherein the surfactant is ammonium lauryl ether sulfate having ethoxy groups of from 1 to 6.

10. A liquid skin cleanser composition according to claims 1, 2, 3, 4, 5, 6, or 7, wherein the surfactant is a mixture of ammonium lauryl sulfate and ammonium lauryl ether sulfate having ethoxy groups of from 1 to 13.

11. A liquid skin cleanser composition according to claims 1, 2, 3, 4, 5, 6, 7, 8 or 9, wherein the surfactant is present at a level of from about 10% to about 25%.

12. A liquid skin cleanser composition according to claims 1, 2, 3, 4, 5, 6, 7, 8 or 9, wherein the surfactant is present at a level of from about 12% to about 22%.

* * * * *